(12) United States Patent
Fruscione-Loizides

(10) Patent No.: US 9,161,854 B2
(45) Date of Patent: Oct. 20, 2015

(54) POSTPARTUM ABDOMINAL SUPPORT

(71) Applicant: THINKING TIGER, LLC, Hamilton, NJ (US)

(72) Inventor: Gia Fruscione-Loizides, Skillman, NJ (US)

(73) Assignee: THINKING TIGER, LLC, Hamilton, NJ (US)

( * ) Notice: Subject to any disclaimer, the term of this patent is extended or adjusted under 35 U.S.C. 154(b) by 65 days.

(21) Appl. No.: 14/195,850

(22) Filed: Mar. 3, 2014

(65) Prior Publication Data
US 2015/0245939 A1    Sep. 3, 2015

(51) Int. Cl.
*A61F 5/00* (2006.01)
*A61F 5/02* (2006.01)
*A61F 13/14* (2006.01)
(Continued)

(52) U.S. Cl.
CPC ... *A61F 5/02* (2013.01); *A61F 5/03* (2013.01); *A61F 13/148* (2013.01); *A41C 1/08* (2013.01)

(58) Field of Classification Search
CPC .............. A61F 5/01; A61F 5/00; A61F 5/02; A61F 5/028; A61F 5/03; A61F 5/002; A61F 13/148; A61F 13/14; A61F 13/00038; A61F 13/13108; A41F 11/16; A41F 9/02; A41C 1/08; A41C 1/02; A41C 1/10; A41C 1/00; A41C 1/006
USPC ......... 2/319, 311–313; 128/96.1, 99.1, 100.1, 128/101.1; 602/5, 19, 23, 24, 63; D24/190–192; 450/95, 155
See application file for complete search history.

(56) References Cited

U.S. PATENT DOCUMENTS

| | | | | |
|---|---|---|---|---|
| 3,115,879 | A | * 12/1963 | Kaplan | 450/117 |
| 3,213,856 | A | * 10/1965 | Gakle | 450/138 |
| 3,442,270 | A | 5/1969 | Steinman | |

(Continued)

FOREIGN PATENT DOCUMENTS

| | | |
|---|---|---|
| CN | 201692113 U | 1/2011 |
| CN | 202437411 U | 9/2012 |
| WO | 2007041243 A2 | 4/2007 |

OTHER PUBLICATIONS

"Postpartum 3 Velcro Straps Reinforced Girdle" http://summerglitz.com.my/postpartum-3-velcro-straps-reinforced-girdle-band-s-m-white.html#.UuBZXftMFkg.
(Continued)

*Primary Examiner* — Kim M Lewis
(74) *Attorney, Agent, or Firm* — Roberts & Roberts, LLP

(57) ABSTRACT

An abdominal support article is disclosed for providing support to a user's abdomen. The abdominal support article includes a continuous tubular support band which encircles a user's abdomen, at least one left-front attachment component and at least one right-front attachment component on the continuous tubular support band, and a plurality of left support straps and right support straps which are to be wrapped around a user and attached to the attachment components of the continuous tubular support band. The at least one left-front attachment component and at least one right-front attachment component are specifically placed such that, in use, the abdominal support article is properly positioned to effectively simulate the bodily support normally provided by the transverse abdominis muscle. The abdominal support article may be incorporated into various support garments such as postpartum and post-surgical support garments and undergarments.

20 Claims, 4 Drawing Sheets

(51) Int. Cl.
*A61F 5/03* (2006.01)
*A41C 1/08* (2006.01)

(56) References Cited

U.S. PATENT DOCUMENTS

| | | |
|---|---|---|
| 3,570,480 A | 3/1971 | Stubbs |
| 3,598,114 A | 8/1971 | Lewis |
| 3,603,316 A | 9/1971 | Lehman |
| 3,752,163 A | 8/1973 | Kaplan |
| 3,812,862 A | 5/1974 | Bernstein |
| 3,920,008 A | 11/1975 | Lehman |
| D278,083 S | 3/1985 | Meier |
| 4,527,566 A | 7/1985 | Abare |
| D296,930 S | 7/1988 | Carabelli |
| D306,364 S | 2/1990 | Hamilton |
| 5,188,585 A | 2/1993 | Peters |
| 5,399,150 A | 3/1995 | Saunders |
| 5,820,575 A | 10/1998 | Cabrera et al. |
| D404,490 S | 1/1999 | Tripolsky |
| 6,585,673 B1 | 7/2003 | Bass |
| 6,921,375 B2 | 7/2005 | Kihara |
| 7,160,262 B2 | 1/2007 | Wicks |
| 7,425,171 B2 | 9/2008 | Maupin |
| D628,300 S | 11/2010 | Caden |
| D660,439 S | 5/2012 | Chen et al. |
| D665,470 S | 8/2012 | Galbraith |
| 8,430,830 B1 | 4/2013 | Ariza |
| 2005/0014451 A1* | 1/2005 | Wicks .......... 450/155 |
| 2005/0181705 A1* | 8/2005 | Maupin .......... 450/155 |
| 2007/0044211 A1* | 3/2007 | Conkle .......... 2/457 |
| 2007/0118062 A1* | 5/2007 | Fleck .......... 602/75 |
| 2010/0100019 A1 | 4/2010 | Chen et al. |
| 2010/0294267 A1* | 11/2010 | Terruso .......... 128/96.1 |
| 2013/0116609 A1 | 5/2013 | Matsuo et al. |
| 2013/0178774 A1 | 7/2013 | Hayes |
| 2013/0344772 A1 | 12/2013 | Fruscione-Loizides |

OTHER PUBLICATIONS

"Style 70 Support Garment," ContourMD.com www.contourmd.com/Style-70-12in-Abdominal-Binder-Adjustable-Panel-Contour.
"Shrinkx Belly Postpartum Belly Band by UpSpring Baby" http://www.shrinkxbelly.com/how-to-wear.
"AbdoMend Support Belt and Strap" http://maternity.about.com/od/thefourthtrimester/tp/4-Post-Partum-Support-Belts-To-Try.htm?p=1.

* cited by examiner

POSTPARTUM ABDOMINAL SUPPORT

BACKGROUND OF THE INVENTION

1. Field of the Invention

The present invention relates to abdominal supports, and more particularly to an abdominal support article for providing support around the abdomen, effectively simulating the bodily support normally provided by the transverse abdominis muscle. The inventive abdominal support article may be incorporated into various support garments such as postpartum and post-surgical support garments and undergarments, and the like.

2. Description of the Related Art

Abdominal supports are well known in the art, and are typically designed to provide support and stability to a user's abdomen. Conventional abdominal supports are often present in the form of a linear panel such as a belt or wrap, which is wrapped around a user's abdomen and secured to itself. Such supports are often bulky and uncomfortable, and are difficult to adjust for a proper supportive fit. The designs of such supports are not conducive to providing customizable levels of support in different areas of the abdomen. Furthermore, while many linear abdominal supports serve to provide external stiffness to a user's abdomen, they fail to provide intra-abdominal pressure which is normally provided by the body's inner abdominal musculature.

U.S. Pat. No. 3,442,270 provides a surgical binder support comprised of a single panel of material which is wrapped around a user's abdomen and secured via Velcro strips 26, 28. Such a binder is not easily adjustable to provide useful support to different users of varying body shapes and support needs. U.S. Pat. No. 3,570,480 provides a linear medical corset to be secured around a user's abdomen. This linear support is wrapped around a user's body and secured to itself via Velcro tapes 32, 34. This configuration also provides difficulty in adjusting the corset to a user's body for proper abdominal support. U.S. Pat. No. 3,598,114 provides an adjustable rib belt which is linear in structure. It features a belt having two ends 12, 14 having tabs 18, 33 which overlap. The linear belt is thus effectively wrapped around a user's abdomen and attached to itself. Optimal support is not achieved with such a configuration. U.S. Pat. No. 3,603,316 discloses an abdominal belt 10 having ends 18 and 20. The ends 18, 20 are brought together and tightened via strips 54, 56, 58, and 60. Thus the linear belt 10 encircles a user's abdomen and is attached to itself. U.S. Pat. No. 3,752,163 provides a linear binder which is adjustable in the direction of their multiple parallel belts 20, 22, 24. These belts are stitched together, to form a panel. The binder is wrapped around a user's abdomen in a linear fashion such that the fastening strip 36 at one end of the binder attaches to section 12 at the other end of the binder. U.S. Pat. No. 3,812,862 discloses a waist-supporting garment having ribbon-like belts encircling the waist, with ends joined to each other by fasteners. U.S. Pat. No. 3,920,008 provides a linear support belt having a primary band and a secondary band, which are placed on top of each other. Each band is wrapped around a user's body and secured to itself. U.S. Pat. No. 6,921,375 provides a lumbar support having an inner belt and an outer belt specifically angled to support a particular region. The inner and outer belts are attached to each other and wrapped around a user's body such that each belt is secured to itself. U.S. Pat. No. 7,160,262 provides a linear abdominal binder which splits apart into two horizontally arranged support bands. The binder is wrapped around a user's body such that the bands are attached to each other at a user's front side. U.S. Pat. No. 8,430,830 provides a postoperative pressure garment which is present in the form of single panel of material which encircles a user's abdomen. The garment has Velcro strips thereon for securing the garment to itself. U.S. Pat. Appln. No. 2013/00116609 provides a linear support having fasteners 31, 32 for attaching the support to itself when wrapped around a user's abdomen. This structure is lacking in its ability adjustment or customization of fit to various abdomen shapes and sizes. U.S. Pat. Appln. No. 2013/0178744 provides a multi-strap lumbar support having a rear panel 123 and parallel support strips which attach to each other around a user's body (see FIGS. 8, 9). Again, this linear configuration requires that the straps of the support are attached to each other. WO/2007/041243 provides a single-strap belt for post caesarian section abdominal support. This single-belt structure requires that the belt's first end 104 and second end 106 are attached to each other.

It is clear that a need exists in the art for an abdominal support article which is capable of providing varying levels of support as needed in different areas of the abdomen. It would be desirable to provide such an abdominal support article which is non-bulky and comfortable while being easily adjustable to provide customized support and tension, and which simulates the support normally provided by a user's inner abdominal musculature, particularly during postpartum or post-surgical recovery. It would further be desirable to provide an abdominal support article which may be easily incorporated into a support garment such as an undergarment or the like.

The present invention solves these problems by providing a specifically designed abdominal support article which is designed to be highly adjustable, thus providing varying levels of abdominal support to a user's desired areas. A key feature of this invention is the presence of a continuous tubular support band to be worn around a user's abdomen. This support band preferably provides compression support to a user's abdomen, while serving as an attachment point for securing support straps around a user's abdomen as described below. Another key feature of this invention is the presence of a plurality of spaced apart support straps which are attached to a rear center panel of the tubular support band. As tension is applied to the support straps, they are laterally stretched from the rear center panel, around the user's sides, across the user's front midline, and are attached to the tubular support band at a desired location on the user's abdomen. Another key feature of this invention is the location of the at least one left-front attachment component and the at least one right-front attachment component on the continuous tubular support band, to which the support straps are attached. As described below, these attachment components of the tubular support band are preferably positioned approximately above the left and right anterior superior iliac spine of the user's pelvis. This landmark ensures that the inventive abdominal support article is properly positioned to provide optimal intra-abdominal support to a user's abdomen, as normally provided by the transverse abdominis muscle. This muscle is the deepest abdominal muscle and a main stabilizer in the abdominal region. When the integrity of the transverse abdominis muscle is compromised, normal body movements such as bending or twisting become difficult. Proper positioning at least one left-front attachment component and at least one right-front attachment component on the continuous tubular support band ensures proper positioning of the abdominal support article on a user's body, thus providing optimal support to the user. The new and useful configuration of the inventive abdominal support satisfies an unmet need in this field by providing enhanced comfort and adjustability, while also providing intra-abdominal support and pressure which is normally provided by the body's inner abdominal musculature.

U.S. Pat. No. 7,425,171 to Maupin provides the closest related art. Maupin provides a post-surgical abdominal binder for female patients. Maupin's invention provides a girdle or the like having cross straps 52, 58. However, it is noted that the structure of Maupin differs significantly from that of the present invention. First, Maupin requires that their cross straps are attached to a centerline of the binder's front section. A second end of each cross strap is then fastened to the binder's side section. Thus, the support provided by Maupin's device is achieved by pulling these centrally attached cross straps outward from a centerline of a user's abdomen, and toward the user's sides where they are attached. As stated in Maupin, their configuration serves to apply pressure to an incision area, optionally with the additional use of a cold pack, to reduce swelling at the incision area. It is clear that Maupin's design and strap placement results in a different type of abdominal support than that provided by the present invention. That is, Maupin's design provides a superficial level support to a surgical incision area, rather than effectively simulating the support and intra-abdominal pressure normally provided by the transverse abdominis muscle as desired by the present invention. The inventive abdominal support article is a clear improvement over what is known and currently used in the art.

SUMMARY OF THE INVENTION

The invention provides an abdominal support article comprising:
a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and
b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to a right-front attachment component, and the first end of each right support strap comprises an attachment component capable of attachment to a left-front attachment component; which left support straps and right support straps each comprise a fabric of two-way elasticity, such that the left support straps are laterally stretchable from the rear center panel, over the left side section of the circular support band, and across a center line of the front section, for attachment to the right-front attachment component of the circular support band, and such that the right support straps are laterally stretchable from the rear center panel, over the right side section of the circular support band, and across a center line of the front section, for attachment the left-front attachment component of continuous circular support band.

The invention also provides a method of providing adjustable support to a user's abdomen, comprising the steps of:
I) providing abdominal support article comprising: a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and
b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to a right-front attachment component, and the first end of each right support strap comprises an attachment component capable of attachment to a left-front attachment component; which left support straps and right support straps each comprise a fabric of two-way elasticity, such that the left support straps are laterally stretchable from the rear center panel, over the left side section of the circular support band, and across a center line of the front section, for attachment to the right-front attachment component of the circular support band, and such that the right support straps are laterally stretchable from the rear center panel, over the right side section of the circular support band, and across a center line of the front section, for attachment the left-front attachment component of continuous circular support band;
II) placing the abdominal support article on a user's body such that it encircles the circumference of a user's abdomen, with the rear center panel being positioned substantially over the user's spine;
III) applying tension to a left support strap, thus laterally stretching said left support strap from the rear center panel, over the left side section of the circular support band, and across a center line of the front section of the support band, and attaching the first end of the left support strap to a right-front attachment component of the support band; and
IV) applying tension to a right support strap, thus laterally stretching said right support strap from the rear center panel, over the left side section of the circular support band, and across a center line of the front section of the support band, and attaching the first end of the right support strap to a left-front attachment component of the support band; thereby providing adjustable support to a user's abdomen.

The invention further provides abdominal support article comprising:
a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to a right-front attachment component, and the first end of each right support strap comprises an attachment component capable of attachment to a left-front attachment component; which left support straps and right support straps each comprise a fabric of two-way elasticity, such that the left support straps are laterally stretchable from the rear center panel, over the left side section of the circular support band, and across a center line of the front section, for attachment to the right-front attachment component of the circular support band, and such that the right support straps are laterally stretchable from the rear center panel, over the right side section of the circular support band, and across a center line of the front section, for attachment the left-front attachment component of continuous circular support band wherein the left support straps and right support straps are attached to the rear center panel in a substantially staggered arrangement relative to each other;

wherein the left support strap attachment components and right support strap attachment components each comprise hook-and-loop fasteners;

wherein the at least one left-front attachment component and the at least one right-front attachment component each comprise hook-and-loop fasteners;

wherein the rear center panel comprises a substantially non-elastic fabric comprising cotton; and wherein the left support straps and right support straps each comprise a fabric of two-way elasticity which is laterally stretchable, said fabric comprising an elastic.

DETAILED DESCRIPTION OF THE INVENTION

Figure 1:
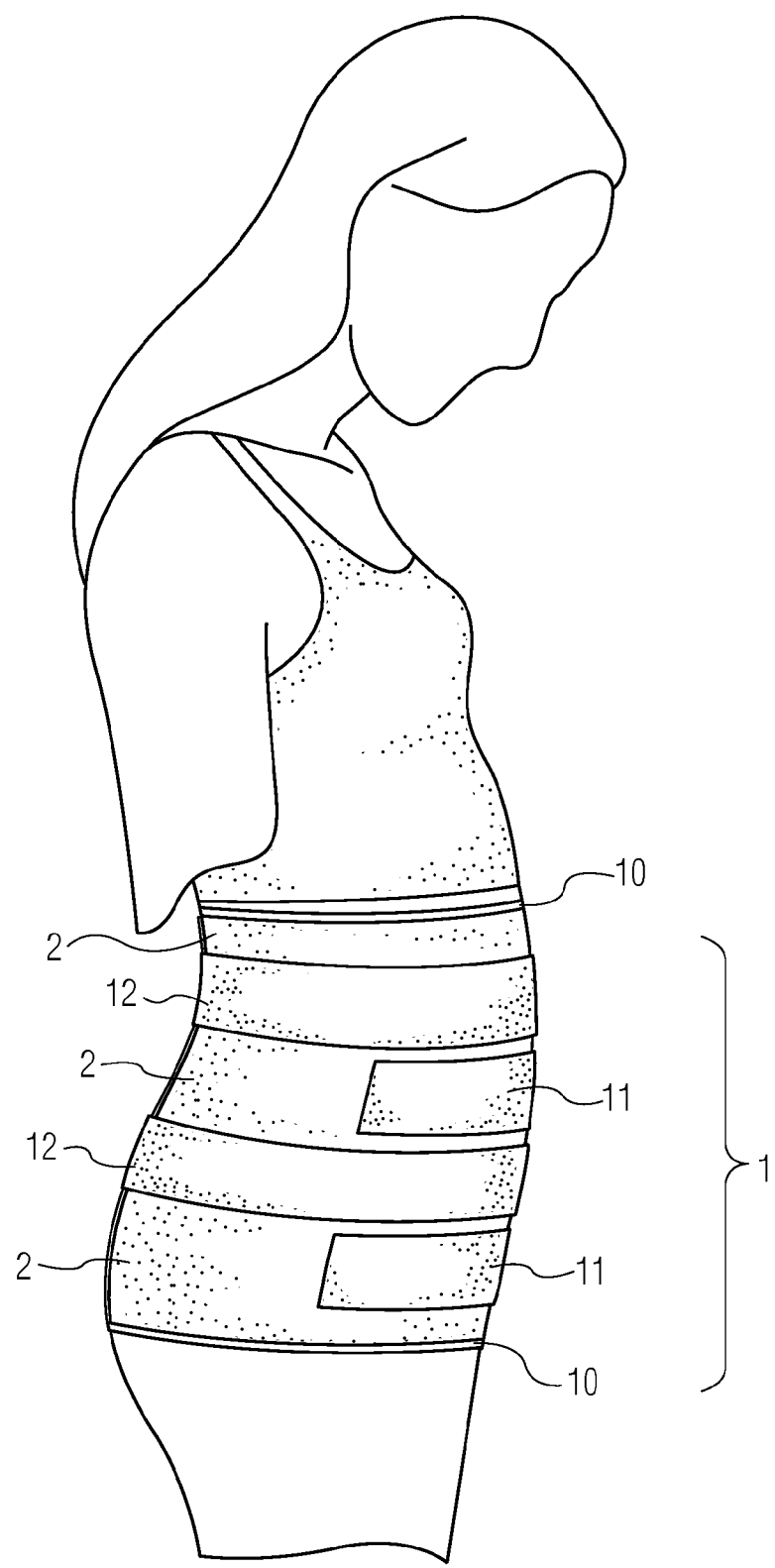
FIG. 1 provides a schematic view of the inventive abdominal support article in use.
Figure 2:
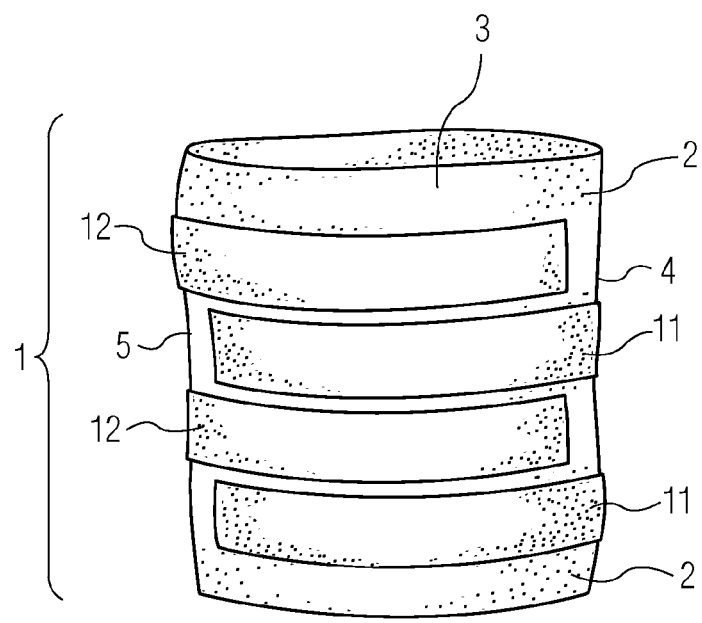
FIG. 2 provides a front schematic view of an abdominal support article of the present invention in a closed orientation.
Figure 3:
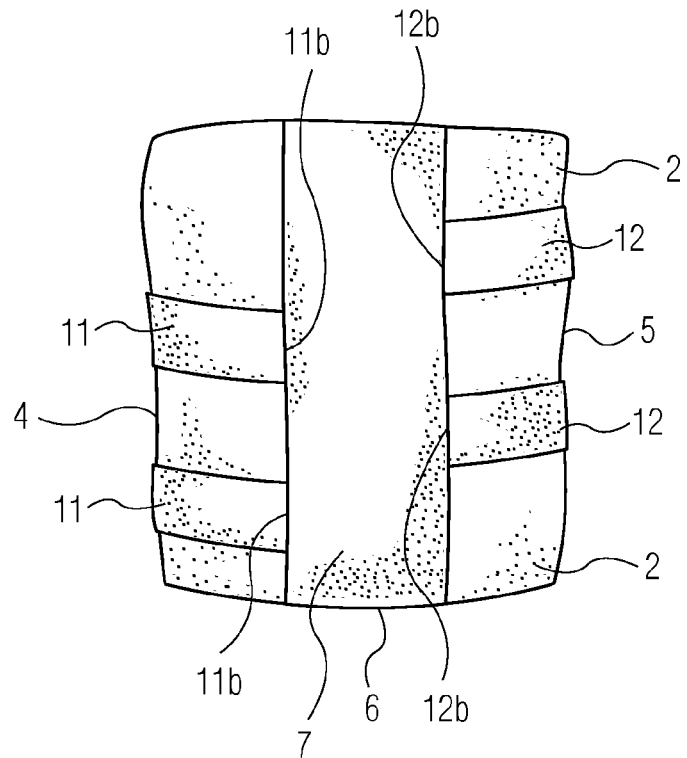
FIG. 3 provides a rear schematic view of an abdominal support article of the present invention in a closed orientation.
Figure 4:
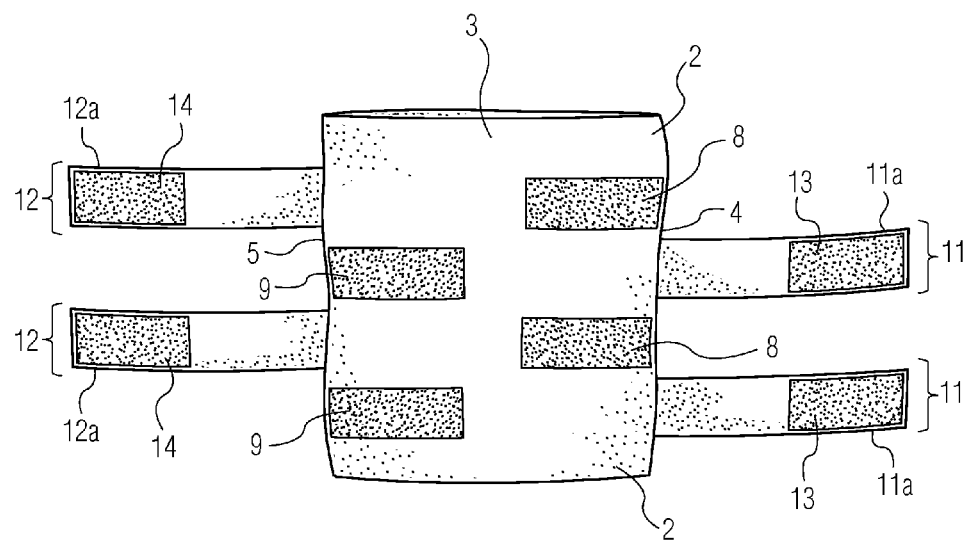
FIG. 4 provides a front schematic view of an abdominal support article of the present invention in an open orientation, having multiple left-front attachment components and multiple right-front attachment components.
Figure 5:
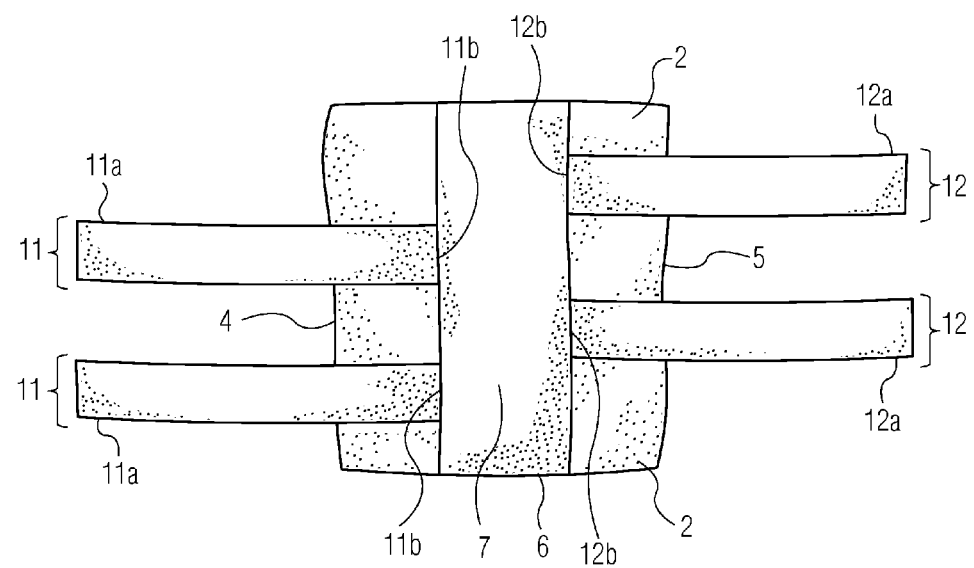
FIG. 5 provides a rear schematic view of an abdominal support article of the present invention in an open orientation.
Figure 6:
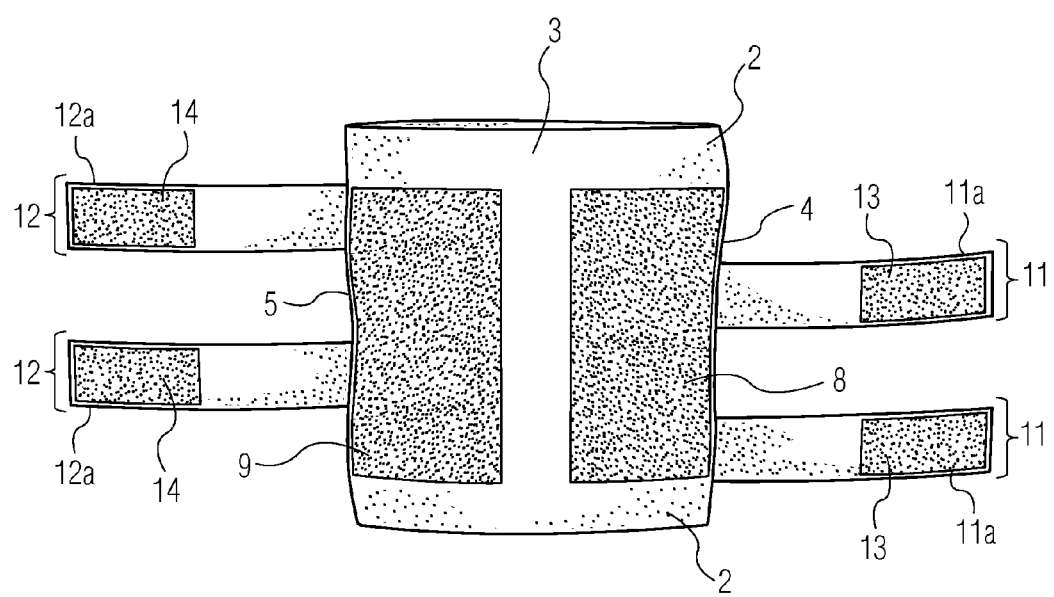
FIG. 6 provides a front schematic view of an abdominal support article of the present invention in an open orientation, having one left-front attachment component and one right-front attachment component.

The present invention provides abdominal support article for providing support to a user's abdomen, effectively simulating the support normally provided by the transverse abdominis muscle. The inventive abdominal support articles are particularly useful in providing abdominal support for rehabilitation after a caesarian section procedure or other abdominal surgery or injury.

As shown in FIGS. 1-6, the inventive abdominal support article 1 first comprises a continuous tubular support band 2. The continuous tubular support band 2 is constructed and designed to be worn around a circumference of a user's abdomen. The support band 2 has a front section 3, a left side section 4, a right side section 5, and a rear section 6. The front section 3, left side section 4, and right side section 5 of the continuous tubular support band 2 preferably comprise a substantially continuous fabric having four-way elasticity, which stretches laterally and longitudinally. Four-way stretch fabrics are known in the art to stretch in both directions. The term four-way elasticity as used herein is intended to indicate a material of four-way stretch, as known in the art. Suitable materials of four-way elasticity for the continuous tubular support band 2 nonexclusively include nylon, elastane, nylon-elastane blends, lycra, lycra blends, and other fabrics or textiles known in the art to be both laterally and longitudinally stretchable, or of four-way stretch, and which are also suitable for clothing applications. In a preferred embodiment, the front section 3, left side section 4, and right side section 5 of the continuous tubular support band 2 preferably comprise a nylon-elastane blend. The rear section 6 of the continuous tubular support band 2 comprises a rear center panel 7, which rear center panel 7 preferably comprises a substantially non-elastic fabric. Suitable substantially non-elastic fabrics non-exclusively include woven materials formed from natural, synthetic, or cellulose fibers. Examples of such materials non-exclusively include one or more of cotton, polyesters, rayon, nylon, wool, and combinations and blends thereof, and other fabrics or textiles known in the art to be substantially non-elastic, and which are also suitable for clothing or garment applications. In a preferred embodiment, the rear center panel 7 comprises cotton. In certain embodiments, the rear center panel 7 may extend through the rear panel 6 of the continuous tubular support band 2 such that said rear center panel 7 extends from an outer surface of the material of the continuous tubular support band 2 to an inner surface of the material of the continuous tubular support band 2. In certain embodiments, the rear center panel 7 may be attached onto an outer surface of the rear panel 6 of the continuous tubular support band 2, wherein the rear panel 6 of the continuous tubular support band 2 is substantially continuous with the front section 3, left side section 4, and right side section 5 of the continuous tubular support band 2, and which rear panel 6 of the continuous tubular support band 2 also comprises a substantially continuous fabric having four-way elasticity, as described above.

The continuous tubular support band 2 further comprises at least one left-front attachment component 8 located between the front section 3 and left side section 4 of the continuous tubular support band 2, and at least one right-front attachment component 9 located between the front section 3 and right side section 5 of the continuous tubular support band 2. The at least one left-front attachment component and the at least one right-front attachment component may each independently comprise any suitable attachment device, nonexclusively including one or more of hook-and-loop fasteners, snaps, clips, hooks, buttons, and the like, and combinations thereof.

In certain embodiments, the abdominal support article 1 comprises one left-front attachment component 8 and one right-front attachment component 9, each comprising a hook-and-loop fastener, such as a single panel of such hook-and-loop fastener material. In certain embodiments, the abdominal support article 1 comprises a plurality of left-front attachment components 8 and a plurality of right-front attachment components 9, each comprising a separate hook-and-loop fastener, such as a tab of such hook-and-loop fastener material.

In certain embodiments, the continuous tubular support band 2 further comprises a border panel 10 attached around a top edge and/or bottom edge of the tubular support band 2, as shown in FIG. 1. The border panel 10 may serve as an area of enhanced elasticity at an edge or border of the abdominal support article 2, such as a waist band or the like. The border panel 10 may comprise a material which is laterally and/or longitudinally stretchable as described herein for other components of this invention. The border panel 10 material may comprise the same material or a different material from that of the continuous tubular support band 2 as described above, or be formed of other fabrics or textiles known in the art to be laterally and/or longitudinally stretchable, and which are also suitable for garment applications.

As shown in FIGS. 1-6, the inventive abdominal support article 1 further comprises a plurality of left support straps 11 and a plurality of right support straps 12. Each of the left support straps 11 has a first end 11a and a second end 11b. The second end 11b of each left support strap 11 is attached, such as by sewing, to the rear center panel 7 of the support band 2. Each of the left support straps 11 are spaced apart and arranged substantially parallel to each other. The right support straps 12 each have a first end 12a and a second end 12b. The second end 12b of each right support strap 12 is attached, such as by sewing, to the rear center panel 7 of the support band 2. Each of the right support straps 12 are spaced apart and arranged substantially parallel to each other. The spaced apart, substantially parallel arrangement of the left support straps 11 and right support straps 12 as described herein allows for the even and continuous application of tension to the abdomen via the abdominal support article 1, when such is desired. In certain embodiments, the left support straps 11 are attached to the rear center panel 7 in a substantially staggered arrangement relative to the right support straps 12, and vice versa. This staggered arrangement allows for an even distribution of tension when pulling the support straps 11, 12 in a back-to-front direction, as described below. An even distribution of tension allows for easier adjustment by a user, and thus increased control over the desired level and location of support provided by abdominal support article 1. This controllability of the provided support is a key feature of the present invention.

The first end 11a of each left support strap 11 comprises an attachment component 13 capable of attachment to a right-front attachment component 9, described above. Similarly, the first end 12a of each right support strap 12 comprises an attachment component 14 capable of attachment to a left-front attachment component 8, described above. The attachment components 13, 14 of the left support strap 11 and the right support strap 12, respectively, may each independently comprise any suitable attachment device, nonexclusively including one or more of hook-and-loop fasteners, snaps, clips, hooks, buttons, and the like, and combinations thereof. In a preferred embodiment, the attachment components 13, 14 each comprise a hook-and-loop fastener.

The left support straps 11 and right support straps 12 each comprise a fabric of two-way elasticity which is laterally stretchable. Suitable materials for the fabric of two-way elasticity nonexclusively include stretch fabrics formed from elastomeric materials. It is known in the art that elastomeric materials generally have a low Young's modulus and high yield strain as compared with other materials. It is also known in the art that stretch fabrics are divided into two categories, namely those of two-way stretch and four-way stretch. Two-way stretch fabrics stretch in one direction, usually from selvedge to selvedge, while four-way stretch fabrics stretch in both directions, crosswise and lengthwise. The term two-way elasticity as used herein is intended to indicate a material of two-way stretch as known in the art. The left support straps 11 and right support straps 12 may each be of the same length or differing lengths. The left support straps 11 and right support straps 12 may each be of the same width or differing widths. The left support straps 11 and right support straps 12 may each comprise the same material or differing materials.

As stated above, in a preferred embodiment the left support straps 11 are laterally stretchable from the rear center panel 7, over the left side section 4 of the circular support band 2, and across a center line of the front section 3, for attachment to the right-front attachment component 9 of the circular support band 2. Similarly, in a preferred embodiment, the right support straps 12 are laterally stretchable from the rear center panel 7, over the right side section 5 of the circular support band 2, and across a center line of the front section 3, for attachment the left-front attachment component 8 of continuous circular support band 2.

When the inventive abdominal support article 1 is worn by a user, it is preferred that the at least one left-front attachment component 8 of the continuous tubular support panel 2 is positioned on a user's abdomen approximately above the left anterior superior iliac spine of the user's pelvis, and the at least one right-front attachment component 9 of the continuous tubular support panel 2 is positioned on the user's abdomen approximately above the right anterior superior iliac spine of the user's pelvis. When configured to exhibit such positioning, the inventive abdominal support article 1 provides enhanced support to a user's abdomen, effectively simulating the abdominal support normally provided by the transverse abdominis, or TVA muscle. This muscle is the deepest abdominal muscle and a main stabilizer in the abdominal region. The transverse abdominis is attached to the body on each side of the spine, via the thoracolumbar fascia of the posterior spine, and fully encircles the abdomen. Its muscular fibers run horizontally, or transversely, across the abdomen. When the abdominal wall is damaged or cut due to situations such as caesarian sections, hysterectomies, hernias, child birth, and the like, body movements such as twisting and bending are diminished. It is an objective of this invention to provide support to the abdomen which simulates the bodily support typically provided by the transverse abdominis muscle, in an effort to assist a user in making normal abdominal movements without causing further injury. As such, it is desired that the inventive abdominal support article 1 be worn by a user in such a way that the left and right support straps 11, 12 run horizontally, or transversely, across the abdomen. As stated above, the support straps 11, 12 are each stretched from the rear center panel 7, around the user's sides, and across the user's front midline. The left support bands 11 are attached to the at least one right-front attachment component 9, which is preferably positioned on a user's abdomen approximately above the left anterior superior iliac spine of the pelvis as described above, and the right support bands 12 are attached to the at least one left-front attachment component 8, which is preferably positioned on a user's abdomen approximately above the left anterior superior iliac spine of the pelvis as described above. This configuration serves to simulate the transverse direction of the fibers of the transverse abdominis muscle.

The present invention may be used in variety of bodily support applications, and should not be limited by those described herein. In certain embodiments, the abdominal support article 1 of this invention provides support to a user's abdomen, such as for postpartum support or post-surgical support. However, the inventive abdominal support article 1 is useful in various other support applications such as therapeutic support, geriatric support, lumbar support, thoracic support, and the like.

The abdominal support article 1 of this invention may be worn on their own, or may be attached to or incorporated into a support garment or the like. This may be done by sewing or by removably attaching the abdominal support article 1 to a support garment by any suitable means. Examples of such support garments include articles of clothing, nonexclusively including undergarments, pants, jeans, shorts, skirts, shirts, blouses, dresses, suits, sleepwear, active wear, sports wear, swimwear, and the like. Support garments may also include body braces or straps, and the like, which are worn in addition to clothing for injury support or other therapeutic support.

In use, the present invention provides a method of providing adjustable support to a user's abdomen. An abdominal support article 1 of the present invention, as described above, is first provided. The abdominal support article 1 is placed on a user's body such that the article 1 encircles the circumference of the user's abdomen. This may be done by any suitable means for wearing the tubular support band 2 of the abdominal support article 1 around the circumference of the user's abdomen, such as stepping into the continuous tubular support band 2 and pulling it over the abdomen. The abdominal support article 1 is preferably positioned such that the rear center panel 7 of the tubular support band 2 is positioned substantially over the user's spine. Using the spine as a landmark will assist in properly positioning the abdominal support article 1 to provide the intra-abdominal support and pressure normally provided by the transverse abdominis muscle, as described above. As stated above, it is preferred that the at least one left-front attachment component 8 of the continuous tubular support panel 2 is positioned on a user's abdomen approximately above the left anterior superior iliac spine of the pelvis, and the at least one right-front attachment component 9 of the continuous tubular support panel 2 is positioned on the user's abdomen approximately above the right anterior superior iliac spine of the pelvis.

Once the abdominal support article is properly positioned, tension is to be applied to at least one left support strap 11. Such tension may be applied by engaging at least one left support strap 11 using suitable means known to those in the art, such as pulling. Such means of applying tension may be determined by those of ordinary skill based on the amount of support needed. In certain embodiments, tension is applied by grasping a left support strap 11 with one's hand, and laterally stretching said left support strap 11. The left support strap 11 is laterally stretched from the rear center panel 7 where its second end 1 lb is attached, over the left side section 4 of the circular support band 2, and across a center line of the front section 3 of the support band 2, wherein the left support strap 11 is attached to a right-front attachment component 9 of the support band 2. In a preferred embodiment, a first end 11a of the left support strap 11 is attached to the right-front attachment component 9 of the support band 2. This attachment may be conducted using any suitable means of attaching the above-described attachment components. In certain embodiments, this attachment is conducted by engaging a hook-and-loop attachment of the first end 11a of the left support strap 11 with a complementary hook and loop attachment of the right-front attachment component 9. Similarly, tension is to be applied to at least one right support strap 12 as well. Such tension may be applied by engaging at least one right support strap 12 using suitable means known to those in the art, such as pulling, and such means of applying tension may be determined by those of ordinary skill based on the amount of support needed. In certain embodiments, tension is applied by grasping a right support strap 12 with one's hand, and laterally stretching said right support strap 12. The right support strap 12 is laterally stretched from the rear center panel 7, where its second end 12b is attached, over the right side section 5 of the circular support band 2, and across a center line of the front section 3 of the support band 2, wherein a first end 12a of the right support strap 12 is attached to a left-front attachment component 8 of the support band 2. In certain embodiments, a first end 12a of the right support strap 12 is attached to the left-front attachment component 8 of the support band 2. This attachment may be conducted using any suitable means of attaching the above-described attachment components. In a preferred embodiment, the attachment is conducted by engaging a hook-and-loop attachment of the first end 12a of the right support strap 12 with a complementary hook and loop attachment of the left-front attachment component 8. In certain embodiments, tension is applied to the left support straps 11 prior to the right support straps 12. In certain embodiments, tension is applied to the right support straps 12 prior to the left support straps 11. In certain embodiments, tension is applied to the left support straps 11 simultaneously with the right support straps 12.

The above abdominal support article 1 and method serve to provide adjustable, comfortable abdominal support which provides intra-abdominal support and pressure normally provided by the body's inner abdominal musculature.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An abdominal support article comprising:
   a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and
   b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to the at least one right-front attachment component, and the first end of each right support strap comprises an attachment component capable of attachment to the at least one left-front attachment component; which left support straps and right support straps each comprise a fabric of two-way elasticity, such that the left support straps are laterally stretchable from the rear center panel, over the left side section of the support band, and across a center line of the front section, for attachment to the at least one right-front attachment component of the continuous tubular support band, and such that the right support straps are laterally stretchable from the rear center panel, over the right side section of the support band, and across a center line of the front section, for attachment to the at least one left-front attachment component of the continuous tubular support band.

2. The abdominal support article of claim 1, wherein when worn by a user, the at least one left-front attachment component is positioned on the user's abdomen approximately above the user's left anterior superior iliac spine of the user's pelvis, and the at least one right-front attachment component is positioned on the user's abdomen approximately above the user's right anterior superior iliac spine of the user's pelvis.

3. The abdominal support article of claim 1 wherein the left support straps are attached to the rear center panel in a substantially staggered arrangement relative to the right support straps.

4. The abdominal support article of claim 1 wherein the left support strap attachment components and right support strap attachment components each independently comprise one or more of hook-and-loop fasteners, snaps, clips, hooks, buttons.

5. The abdominal support article of claim 1 wherein the at least one left-front attachment component and the at least one right-front attachment component each independently comprise one or more of hook-and-loop fasteners, snaps, clips, hooks, buttons.

6. The abdominal support article of claim 5 wherein the at least one left- front attachment component comprising one left-front attachment component and the at least one right-front attachment component comprises one right-front attachment component, wherein each of the left-front attachment component and the right-front attachment component comprises a hook-and-loop fastener.

7. The abdominal support article of claim 5 wherein the at least one left-front attachment component comprises a plurality of left-front attachment components and wherein the at least one right-front attachment component comprises a plurality of right-front attachment components, wherein each of the left-front attachment components and the right-front attachment components comprise a hook-and-loop fastener.

8. The abdominal support article of claim 1 wherein the a substantially non-elastic fabric of the rear center panel comprises one or more of cotton, polyesters, rayon, nylon, wool, and combinations or blends thereof.

9. The abdominal support article of claim 1 wherein the fabric of two-way elasticity of each of the left support straps and the right support straps comprises one or more of an elastic, elastane, elastane blends, and combinations thereof.

10. A support garment comprising the abdominal support article of claim 1.

11. The support garment of claim 10 which comprises an undergarment.

12. A method of providing adjustable support to a user's abdomen, comprising the steps of:
I) providing abdominal support article comprising: a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and
b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to the at least one right-front attachment component, and the first end of each right support strap comprises an attachment component capable of attachment to the at least one left-front attachment component; which left support straps and right support straps each comprise a fabric of two-way elasticity, such as the left support straps are laterally stretchable from the rear center panel, over the right side section of the support band, and across a center, and the front section, for attachment to the at least one right-front attachment component of the continuous tubular support band, and such that the right support straps are laterally stretchable from the rear center panel, over the right side section of the support band, and across a center line of the front section, for attachment to the at least one left-front attachment component of the continuous tubular support band;
II) placing the abdominal support article on a user's body such that it encircles the circumference of a user's abdomen, with the rear center panel being positioned substantially over the user's spine;
III) applying tension to a left support strap, thus laterally stretching said left support strap from the rear center panel, over the left side section of the support band, and across a a center line of the front section of the support band, and attaching the first end of the left support strap to the at least one right-front attachment component of the support band; and
IV) applying tension to a right support strap, thus laterally stretching said right support strap from the rear center panel, over the left side section of the support band, and across a center line of the front section of the support band, and attaching the first end of the right support strap to the at least one left-front attachment component of the support band; thereby providing adjustable support to a user's abdomen.

13. The method of claim 12 wherein steps III and IV are conducted substantially simultaneously.

14. The method of claim 12 wherein, in step II, the abdominal support article is placed on a user's body such that the at least one left-front attachment component is positioned on the user's abdomen approximately above the user's left anterior superior iliac spine of the user's pelvis, and the at least one right-front attachment component is positioned on the user's abdomen approximately above the user's right anterior superior iliac spine of the user's pelvis.

15. The method of claim 12 wherein the left support straps of the abdominal support article are attached to the rear center panel in a substantially staggered arrangement relative to the right support straps.

16. An abdominal support article comprising:
a) a continuous tubular support band to be worn around a circumference of a user's abdomen, said support band having a front section, a left side section, a right side section, and a rear section, which front section, left side section, and right side section comprise a continuous fabric having four-way elasticity, and which rear section comprises a rear center panel comprising a substantially non-elastic fabric; the continuous tubular support band further comprising at least one left-front attachment component located between the front section and left side section, and at least one right-front attachment component located between the front section and right side section; and
b) a plurality of left support straps, each having a first end and a second end, the second end of each left support strap being attached to the rear center panel of the support band, the left support straps being spaced apart and arranged substantially parallel to each other, a plurality of right support straps, each having a first end and a second end, the second end of each right support strap being attached to the rear center panel of the support band, the right support straps being spaced apart and arranged substantially parallel to each other, and wherein the first end of each left support strap comprises an attachment component capable of attachment to the at least one right-front attachment component, and the first end of each right support strap comprises an attachment component capable of attachment to the at least one left-front attachment component; which left support straps and right support straps each comprise a fabric of two-way elasticity, such that the left support straps are laterally stretchable from the rear center panel, over the left side section of the support band, and across a center line of the front section, for attachment to the at least one right-front attachment component of the continuous tubular support band, and such that the right support straps are laterally stretchable from the rear center panel, over the right side section of the support band, and across a center line of the front section, for attachment to the at least one left-front attachment component of the continuous tubular support band wherein the left support straps and right support straps are attached to the rear center panel in a substantially staggered arrangement relative to each other;
wherein the left support strap attachment components and right support strap attachment components each comprise hook-and-loop fasteners;
wherein the at least one left-front attachment component and the at least one right-front attachment component each comprise hook-and-loop fasteners;
wherein the a substantially non-elastic fabric of the rear center panel comprises cotton; and
wherein the fabric of two-way elasticity of each of the left support straps and the right support straps comprises an elastic.

17. The abdominal support article of claim 16, wherein when worn by a user, the at least one left-front attachment component is positioned on the user's abdomen approximately above the user's left anterior superior iliac spine of the user's pelvis, and the at least one right-front attachment component is positioned on the user's abdomen approximately above the user's right anterior superior iliac spine of the user's pelvis.

18. The abdominal support article of claim 16 wherein the left support straps and right support straps are attached to the rear center panel in a substantially staggered arrangement relative to each other.

19. A support garment comprising the abdominal support article of claim 16.

20. The support garment of claim 19 which comprises an undergarment.

\* \* \* \* \*